United States Patent [19]

Kennedy

[11] Patent Number: 5,102,983
[45] Date of Patent: Apr. 7, 1992

[54] PROCESS FOR PREPARING FOAMED, BIOABSORBABLE POLYMER PARTICLES

[75] Inventor: John Kennedy, Stratford, Conn.

[73] Assignee: United States Surgical Corporation, Norwalk, Conn.

[21] Appl. No.: 503,264

[22] Filed: Apr. 2, 1990

[51] Int. Cl.$^5$ .................. C08G 63/08; A61K 31/74; A61K 9/14; A01N 25/02
[52] U.S. Cl. ........................... 528/354; 424/43; 424/78.3; 424/486; 528/480; 523/113
[58] Field of Search ............. 528/354, 480; 424/78, 424/486, 43; 523/113

[56] References Cited

U.S. PATENT DOCUMENTS

| | | | |
|---|---|---|---|
| 3,812,224 | 5/1974 | Smith et al. | 264/28 |
| 3,882,858 | 5/1975 | Klemm | 128/92 |
| 4,118,449 | 10/1978 | Rinde | 264/41 |
| 4,186,448 | 2/1980 | Brekke | 128/92 |
| 4,430,451 | 2/1984 | Young et al. | 521/64 |
| 4,519,909 | 5/1985 | Castro | 521/64 |
| 4,535,485 | 8/1985 | Ashman et al. | 128/92 |
| 4,547,390 | 10/1985 | Ashman et al. | 128/92 |
| 4,643,735 | 2/1987 | Hayes et al. | 525/937 |
| 4,663,447 | 5/1987 | Yamazaki et al. | 428/402 |
| 4,673,695 | 6/1987 | Aubert et al. | 521/64 |
| 4,693,986 | 9/1987 | Vit et al. | 264/117 |
| 4,810,775 | 3/1989 | Bendix et al. | 528/480 |
| 4,822,534 | 4/1989 | Lencki et al. | 264/4.3 |
| 4,822,535 | 4/1989 | Ekman et al. | 264/4.3 |
| 4,933,105 | 6/1990 | Fong | 424/462 |
| 4,940,734 | 7/1990 | Ley et al. | 521/89 |
| 5,015,423 | 5/1991 | Eguchi et al. | 264/9 |
| 5,015,667 | 5/1991 | Yoshimura et al. | 521/58 |
| 5,019,400 | 5/1991 | Gombotz et al. | 424/501 |

FOREIGN PATENT DOCUMENTS

| | | |
|---|---|---|
| 265906A2 | 5/1988 | European Pat. Off. |
| 274898 | 7/1988 | European Pat. Off. |

OTHER PUBLICATIONS

NASA Tech Briefs, Sep. 1987, p. 50.
J. Microencapsulation, 1988; vol. 5, No. 2, 147–157.

*Primary Examiner*—John Kight, III
*Assistant Examiner*—John M. Cooney, Jr.
*Attorney, Agent, or Firm*—Thomas R. Bremer; Peter G. Dilworth; Rocco S. Barrese

[57] ABSTRACT

A process is provided for preparing foamed, bioabsorbable polymer particles employing a freeze-drying operation.

21 Claims, No Drawings

PROCESS FOR PREPARING FOAMED, BIOABSORBABLE POLYMER PARTICLES

BACKGROUND OF THE INVENTION

This invention relates to a process for preparing foamed, bioabsorbable polymer particles, e.g., spheroidal particulates or beads, employing a freeze-dry operation. The particles are useful, inter alia, in medical diagnostic procedures such as mammography and in the repair of damaged or defective bone.

The medical use of polymer particles including those of the bioabsorbable variety are known, inter alia, from U.S. Pat. Nos. 3,882,858; 4,535,485; 4,547,390; 4,643,735; and, 4,663,447. There has been an increase in interest in utilizing bioabsorbable polymer particles to facilitate bone or fibrous tissue repair/reconstruction. The particles can be readily conformed to the shape of defects present in bone or fibrous tissue. Additionally, bioabsorbable polymer particles serve as excellent vehicles for the delivery of drugs, growth factors and/or other biologically active substances to surrounding bone or tissue into which the particles are incorporated.

SUMMARY OF THE INVENTION

It is an object of the present invention to provide a process for preparing foamed, bioabsorbable polymer particles.

It is another object of the invention to provide foamed, bioabsorbable polymer particles which are useful, inter alia, in the repair of bone or fibrous tissue.

It is still another object of the present invention to provide a system for the delivery of bioactive substances such as medicinals, drugs, growth factors, etc., to damaged bone or tissue to promote the healing thereof.

Yet another object of the present invention is to improve control over sizes of foamed bioabsorbable polymer particles which are prepared.

These and other objects of the present invention are achieved by the process for preparing foamed, bioabsorbable polymer particles which comprises:

a) dissolving a foam-forming bioabsorbable polymer in a solvent therefor to form a solution of the polymer;

b) introducing relatively small, discrete quantities of the thus-formed polymer solution into a liquid which is immiscible with the solvent and which freezes the polymer solution on contact therewith to provide particles of frozen polymer solution in the liquid;

c) recovering the particles of frozen polymer solution from the liquid; and, d) removing solvent from the particles of frozen polymer solution under vacuum to provide substantially solvent-free, foamed, bioabsorbable polymer particles.

The foamed particles of this invention can be provided essentially free of solvent, a significant advantage over known processes of making foamed particles which employ organic blowing or foaming agents since it is essential that foamed particles for internal medical use contain little or no residual foaming agent. Furthermore, low processing temperatures can be utilized in the foamed particle manufacturing process of the present invention thus allowing incorporation into the polymer of medicinals, drugs, growth factors, radiopaque substances, and the like, which cannot tolerate high processing temperatures. Additionally, improved control of the overall sizes of foamed bioabsorbable polymer particles is provided, i.e. the particles can be prepared with sufficiently uniform or narrow range of sizes.

DESCRIPTION OF THE PREFERRED EMBODIMENTS

A. Preparing the Solution of Bioabsorbable Polymer

The first step in the present invention involves preparing a solution of a bioabsorbable foam-forming polymer in a suitable solvent to form a solution of the polymer. The polymer can be derived from polyglycolic acid, glycolide, lactic acid, lactide, dioxanone, e-caprolactone, trimethylene carbonate, etc., and various combinations of these and related monomers. Polymers of this type are known in the art, principally as materials for the fabrication of such surgical devices as sutures, wound clips, and the like, as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gliding et al., "Biodegradable polymers for use in surgery—polyglycolic/poly(lactic acid) homo- and co-polymers": 1, *Polymer*, Volume 20, pages 1459–1464 (1979), and D. F. Williams (ed.), *Biocompatibility of Clinical Implant Materials*, Vol. II, ch. 9: "Biodegradable Polymers" (1981). Copolymers of glycolide and lactide with or without additional monomers are preferred and of these glycolide-lactide copolymers are most preferred.

The solvent can be any solvent which is capable of dissolving the selected bioabsorbable polymer with the resulting polymer solution freezing solid when contacted with a freezing liquid which is immiscible with the solvent. More particularly, such solvents should possess a vapor pressure such that at or below the freezing point of the solvent, evaporation or sublimation can take place in vacuo. Suitable solvents include those selected from the group consisting of t-butanol, benzene, p-dioxane, p-xylene, 1,2-dibromoethane, morpholine, dimethylsulfoxide, bromoform, hexafluoroisopropanol (HFIP), hexafluoroacetone sesquihydrate (HFAS), and mixtures thereof, with p-dioxane and/or benzene being preferred. HFIP has also been employed advantageously with high glycolide-containing glycolide-lactide copolymers, and HFAS has been effectively used with polyglycolic acid. A summary of the properties of these solvents is presented in the following table:

| Solvent | Melting Point °C. | Vapor Pressure (Torr) at 25° C. | Estimated Vapor Pressure (Torr) At Melting Point |
|---|---|---|---|
| t-Butanol | 26.8 | 42.0 | |
| Benzene | 5.5 | 95.2 | 35.9 |
| p-Dioxane | 11.8 | 37.1 | 20.6 |
| p-Xylene | 13.5 | 8.7 | 4.3 |
| 1,2-Dibromoethane | 9.7 | 7.8 | 2.0 |
| Morpholine | −3.1 | 10.1 | 1.8 |
| Dimethylsulfoxide | 18.5 | 0.6 | |
| Bromoform | 8.0 | 5.9 | 2.3 |
| HFIP | −4 | 102[1] | |
| HFAS | 21 | | |

The concentration of the polymer in the solvent is controlled, depending upon the desired ultimate density of the particles that are formed. The solution must not become too viscous or gel. Generally, the amount of the polymer in the solution can vary over a wide range, such as from about 1 to about 20% by weight, with approximately 5 to about 15% by weight being preferred. Typically, the lower end of the concentration range is defined by the acceptable bead densities, i.e., too low a concentration will result in an unacceptably low density product. The upper limit of the concentration range is typically set by viscosity considerations, i.e. too high a concentration may result in the formation of a gel or a solution too viscous to efficiently process as described below.

At the time of preparing the polymer solution, one or more bioactive substances can be incorporated into the solution in the customary amounts so that at the conclusion of the polymeric particle manufacturing process herein, the particles will contain a predetermined amount of one or more such substances.

Thus, it is within the scope of this invention to incorporate one or more medico-surgically useful substances into the particles, e.g., those which accelerate or beneficially modify the healing process when particles are applied to a surgical repair site. So, for example, the foamed bioabsorbable polymer particles can carry a therapeutic agent which will be deposited at the repair site. The therapeutic agent can be chosen for its antimicrobial properties, capability for promoting repair or reconstruction and/or new tissue growth or for specific indications such as thrombosis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the particles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

Similarly, where the foamed particles are to be employed in diagnosis, a radiopaque material, e.g., a substance such as a barium or calcium salt or a dye such as a medically improved violet dye can be incorporated into the particles at the time of forming the polymer solution.

B. Freezing the Solution of Bioabsorbable Polymer

After the solution of bioabsorbable polymer has been prepared, the solution is introduced in relatively small, discrete quantities into a freezing liquid which is immiscible with the solvent to provide particles of frozen polymer solution in the liquid. The discrete quantities of polymer solution are preferably provided as drops thereof, with the solution being introduced drop-by-drop into the freezing liquid from an orifice possessing a diameter calculated to provide drops, or spheroids, of predetermined average diameter, or by other suitable atomization means. In general, the average droplet size of polymer solution can vary from about 100 to about 700 microns, with from about 200 to about 600 microns being preferred. However, particles or beads of any size may be produced according to the present process. For example, particles having sizes of about 7000 to 8000 microns can be satisfactorily prepared with the present process.

The freezing liquid can be, e.g., liquid nitrogen, mixtures of solid carbon dioxide and a liquid such as acetone, pentane, etc. In general, the temperature of the freezing liquid is advantageously at least about 10° C. below the freezing temperature of the polymer solution. The lower the temperature of the freezing liquid, the faster the polymer solution will freeze solid therein. It is desirable to maintain a certain particle configuration, e.g., spheres upon freezing, and therefore rapid, even instantaneous freezing is called for. This can be conveniently achieved employing a freezing liquid such as liquid nitrogen.

C. Recovering the Particles of Frozen Bioabsorbable Polymer Solution

The particles of frozen bioabsorbable polymer solution can be recovered from the freezing liquid employing any suitable means, e.g., draining, straining, filtering, decanting or centrifuging, and the like. This operation is conducted at or below the melting point of the frozen polymer particles to maintain the particles in the frozen state before and during the vacuum solvent removal operation.

D. Removing Solvent From the Frozen Particles of Bioabsorbable Polymer Solution

Solvent is removed from the frozen particles of bioabsorbable polymer solution at reduced pressure, i.e., under freeze-drying conditions, to provide substantially solvent-free particles of foamed polymer. This removal of solvent by freeze-drying is in itself a well known type of procedure, the details of which need not be repeated here. For example, a freeze-drying procedure such as described at pages 17-26 to 17-28 of *Chemical Engineers' Handbook*, fourth edition, John H. Perry (editor), McGraw-Hill Book Company, may be followed. In general, a vacuum, e.g., a pressure of less than about 10 torr and preferably less than about one torr, is applied to the frozen polymer particles at their frozen temperature depending upon the solvent used so that the solvent which had been frozen along with the polymer will evaporate, leaving behind foamed bioabsorbable polymer particles. This evaporation by freeze-drying must be carried out to a sufficient degree, otherwise a solution will reform from the frozen foam when the particles are warmed above the freezing point of the initial polymer solution.

The thus-formed particles of foamed polymer can be maintained under vacuum for widely varying periods of time, e.g., from about 10 to about 15 hours, provided that substantially all of the solvent has evaporated. The temperature can then be raised at a reduced pressure to facilitate removal of any minor amounts of residual solvent. Preferably the temperature is allowed to slowly rise to about 20° C. and higher, depending upon the thermal stability of the polymer and any additives.

The Foamed Bioabsorbable Polymer Particles

The particles prepared in accordance with the foregoing process are advantageously spherical or ellipsoidal in shape ("beads") and will possess the desired particle size distribution, e.g. average sizes ranging from about 100-700 microns in diameter, preferably about 200 to 600 microns in diameter. However, particles having sizes of at least about 1,680 microns can also be satisfactorily prepared with the foregoing process. The particles can be easily molded and packed into shapes conforming to defects in bone and fibrous tissue. The foamed particles are characterized by possessing low densities, e.g., of about 0.01 to about 0.30 g/cc, as compared to a starting density of 1.1 to 1.4 for typical glycolide and lactide polymers and copolymers. The density achieved may be controlled by selecting a suitable initial concentration of polymer in solvent. Moreover, the particles tend to be highly porous with pore sizes ranging from about 4 to about 10 microns. When placed in water at about 37° C., the foamed particles float and do not appear to take up any water.

The particles or beads formed of the foamed polymer resin can be used as filler in a surgical prosthesis, i.e. for implantation in a cavity provided in bone or fibrous tissue to encourage regrowth and regeneration of the tissue. The particles of the foamed bioabsorbable resin are absorbed by the body at a predictable rate allowing tissue or bony ingrowth as absorption takes place. The rate of absorption is characteristic of the polymer utilized. Thus, e.g., a glycolide-lactide copolymer will often completely resorb within six months in contrast to about two years for polylactide homopolymer. The foamed, bioabsorbable polymer particles are readily molded to fill cavities or other contours. The beads can be heated to softening temperature, e.g., to about 60° C., at which temperature they can be worked and shaped.

The present invention will be described in greater detail with reference to the following examples:

EXAMPLE 1

An 18/82 glycolide-L-lactide copolymer (10 grams) was dissolved in 100 ml of p-dioxane solvent to provide a 10 percent solution of the copolymer. Fifty drops of solution were introduced drop-by-drop using a pipette into a vessel containing 0.125 liters of liquid nitrogen at $-197°$ C. and at room pressure. The droplets ranged in size from 100 to 700 microns. After freezing of the copolymer solution, the frozen particles were recovered and placed in a freeze-drying chamber which was subsequently sealed and placed under vacuum to evaporate the solvent from the particles of frozen polymer solution. The chamber was evacuated to less than 10 Torr and maintained at this level of vacuum for about 10–15 hours at a temperature of 0° C. The temperature level was thereafter permitted to slowly rise to 20° C. The foamed, bioabsorbable glycolide-lactide copolymer particles were then removed and observed to have a spongy, porous appearance.

EXAMPLE 2

The steps of Example 1 were repeated with a 10% solution of a 25/75 glycolide-L-lactide copolymer in p-dioxane solvent. Droplets of the solution were pipetted into a liquid nitrogen-containing chamber using a 20 gauge syringe. The frozen beads were collected from the liquid nitrogen by allowing the liquid nitrogen to boil off. The p-dioxane solvent was removed from the frozen beads by freeze drying at a pressure of about 10 torr. The beads recovered were retained on a 10 mesh screen and some beads appeared to be hollow at their core.

What is claimed is:

1. Process for preparing foamed, bioabsorbable polymer particles which comprises:

a) dissolving a foam-forming bioabsorbable polymer in a solvent therefor to form a solution of the polymer;
b) introducing relatively small, discrete quantities of the thus-formed polymer solution into a liquid which is immiscible with the solvent and which freezes the polymer solution on contact therewith to provide particles of frozen polymer solution in the liquid;
c) recovering the particles of frozen polymer solution from the liquid; and,
d) removing solvent from the particles of frozen polymer solution under vacuum to provide substantially solvent-free, foamed, bioabsorbable -polymer particles.

2. The process of claim 1 further comprising:
e) raising the temperature of the particles resulting from step (d) to remove any residual solvent.

3. The process of claim 1, wherein said discrete quantities of solution are in the form of drops thereof having an average diameter of from about 100 to about 700 microns.

4. The process of claim 3, wherein said average diameter is from about 200 to about 600 microns.

5. The process of claim 1, wherein said liquid is selected from the group consisting of liquid nitrogen, and mixtures of solid carbon dioxide and a liquid.

6. The process of claim 1, wherein said polymer is derived from the group consisting of polyglycolic acid, glycolide, lactic acid, lactide, dioxanone, e-caprolactone, trimethylene carbonate, and mixtures thereof.

7. The process of claim 6, wherein said polymer is a glycolide-lactide copolymer.

8. The process of claim 1, wherein said solvent is selected from the group consisting of t-butanol, benzene, p-dioxane, p-xylene, 1,2-dibromoethane, morpholine, dimethylsulfoxide, bromoform, hexafluoroisopropanol, hexafluoroacetone sesquihydrate, and mixtures thereof.

9. The process of claim 1, wherein pressure of said vacuum is less than about 10 torr.

10. The process of claim 9, wherein said pressure is less than about one torr.

11. The process of claim 9, wherein said frozen polymer particles are held under said vacuum for about 10 to about 15 hours.

12. The process of claim 3, wherein the particles have a density of about 0.01 g/cc to about 0.30 g/cc.

13. The process of claim 1, wherein the bioabsorbable polymer is dissolved in the solvent in an amount of about 1 to about 20% by weight.

14. The process of claim 13, wherein the amount of the bioabsorbable polymer dissolved in the solvent is from about 5 to 15% by weight.

15. The process of claim 1, wherein the particles of frozen polymer solution are immediately recovered from the freezing liquid and then immediately subjected to the vacuum to remove the solvent therefrom.

16. The process of claim 1, wherein temperature of the freezing liquid is at least about 10° C. below freezing temperature of the polymer solution.

17. The process of claim 1, wherein the particles of frozen polymer solution are recovered at or below melting point thereof to maintain the particles in frozen state.

18. The process of claim 1, wherein the particles of frozen polymer solution are recovered by draining, straining, filtering, decanting or centrifuging.

19. The process of claim 2, wherein the temperature is allowed to slowly rise at least about 20° C.

20. The process of claim 3, wherein the particles each comprise pores of size ranging from about 4 to about 10 microns.

21. The process of claim 1, wherein the relatively small, discrete quantities of the polymer solution are introduced into the liquid on a drop-by-drop basis.

* * * * *